United States Patent
Chung et al.

(10) Patent No.: US 7,771,620 B2
(45) Date of Patent: Aug. 10, 2010

(54) POLYELECTROLYTE COMPOSITION FOR HUMIDITY SENSER, POLYELECTROLYTE INK AND PREPARATION METHOD OF POLY ELECTROLYTE MEMBRANE FOR SENSOR BY INKJET PRINTING

(75) Inventors: Kwang Choon Chung, Seoul (KR); Myoung Seon Gong, Seoul (KR); Jae Joon Shim, Yongin-si (KR)

(73) Assignee: Haeun Chemtec Co., Ltd, Kyungki-do (KR)

(*) Notice: Subject to any disclaimer, the term of this patent is extended or adjusted under 35 U.S.C. 154(b) by 923 days.

(21) Appl. No.: 10/567,976

(22) PCT Filed: Aug. 2, 2004

(86) PCT No.: PCT/KR2004/001943

§ 371 (c)(1),
(2), (4) Date: Oct. 31, 2006

(87) PCT Pub. No.: WO2005/014700

PCT Pub. Date: Feb. 17, 2005

(65) Prior Publication Data

US 2007/0182791 A1    Aug. 9, 2007

(30) Foreign Application Priority Data

Aug. 12, 2003    (KR)    ........... 10-2003-0055604

(51) Int. Cl.
*H01B 1/00* (2006.01)
*H01C 7/00* (2006.01)
*B01J 49/00* (2006.01)

(52) U.S. Cl. .................... 252/500; 338/35; 521/25

(58) Field of Classification Search ............... 252/500; 338/35; 521/25
See application file for complete search history.

(56) References Cited

U.S. PATENT DOCUMENTS

| | | | | |
|---|---|---|---|---|
| 4,119,581 A | * | 10/1978 | Rembaum et al. | 521/27 |
| 4,696,796 A | * | 9/1987 | Oka et al. | 422/88 |
| 4,835,206 A | * | 5/1989 | Farrar et al. | 524/457 |
| 4,889,561 A | * | 12/1989 | Sugihara et al. | 536/80 |

(Continued)

FOREIGN PATENT DOCUMENTS

JP    62-245149    10/1987

(Continued)

OTHER PUBLICATIONS

Gamota et al., "Printed Organic and Molecular Electronics," p. 315 (2004).*

*Primary Examiner*—Mark Kopec
*Assistant Examiner*—Jaison P Thomas
(74) *Attorney, Agent, or Firm*—The Webb Law Firm (57) ABSTRACT

This invention relates to a polyelectrolyte composition for a humidity sensor, polyelectrolyte ink and a preparation method of a polyelectrolyte membrane for a humidity sensor by inkjet printing. The polyelectrolyte composition according to this invention is composed of polyelectrolyte, crosslinking agent and organic solvent comprising a single component or in the form of a mixture of two or more solvents such as alcohols. The object of this invention is to provide a polyelectrolyte composition and a polyelectrolyte ink composition suitable for humidity sensor and a preparation method for a reliable humidity sensor with uniform thickness achieved through inkjet printing.

22 Claims, 2 Drawing Sheets

U.S. PATENT DOCUMENTS

| | | | |
|---|---|---|---|
| 5,546,802 | A | 8/1996 | Yoshimura et al. |
| 6,568,265 | B2 | 5/2003 | Shibue et al. |
| 2003/0056571 | A1 | 3/2003 | Shibue et al. |
| 2003/0078185 | A1* | 4/2003 | Norenberg et al. .......... 510/475 |

FOREIGN PATENT DOCUMENTS

| | | |
|---|---|---|
| JP | 62-247239 | 10/1987 |

* cited by examiner

POLYELECTROLYTE COMPOSITION FOR HUMIDITY SENSER, POLYELECTROLYTE INK AND PREPARATION METHOD OF POLY ELECTROLYTE MEMBRANE FOR SENSOR BY INKJET PRINTING

TECHNICAL FIELD

The present invention relates to a polyelectrolyte composition for humidity-sensitive membrane of humidity sensor, a polyelectrolyte ink prepared therefrom, and a process for preparing humidity sensor by injet printing method to form humidity-sensitive membrane. More specifically, the present invention provides a polyelectrolyte ink, which can form a humidity-sensor membrane by dissolving a polyelectrolyte in a solvent to prepare the solution of a polyelectrolyte composition, which is then applied to an inkjet printer. Further, the present invention also provides a process for preparing humidity sensor by printing with the polyelectrolyte ink prepared using an inkjet printer and then treating the printed matter with heat to form a humidity-sensitive membrane onto various electrodes.

BACKGROUND ART

Prior processes for forming the humidity-sensitive membrane generally use dipping, spin coating, spraying and dispenser spreading methods, and as the base material various materials including hard base materials such as alumina or epoxy, and soft base materials such as polyimides have been used depending on the purpose of use.

The dipping method is a method which comprises attaching lead wire to the base material onto which the electrode is formed, followed by fixing to a jig, dipping vertically to the humidity-sensitive membrane for a certain period, then raising to make level, drying and then thermally reacting to form the humidity-sensitive membrane.

The spin coating method is a method which has been frequently used in semiconductor procedures, and forms the humidity-sensitive membrane onto electrodes by dropping polyelectrolyte solution onto the rotating electrodes.

The spray method is a method which forms the humidity-sensitive membrane by spraying polyelectrolyte solution through nozzle to spread onto the electrodes.

The dispenser spreading method is a method which forms the humidity-sensitive membrane onto electrodes by injecting polyelectrolyte solution in several microliter units via a microinjector.

At the present time, although the above methods have been widely used, they have disadvantages including complicated procedures, relatively long process times, a loss of raw materials, low yields and high expenses. Particularly, since it is very difficult to from the humidity-sensitive membrane having a certain thickness in the state that the electrode has already been formed in a substantial thickness, it is very difficult to control the properties required to have accuracy. Further, the dipping method as a most widely used method can be readily applied to the hard base materials but has a great difficulty in spreading the humidity-sensitive membrane onto the soft base materials.

DISCLOSURE OF THE INVENTION

The above-mentioned problems can be solved by a process for forming the humidity-sensitive membrane using inkjet printer.

The process for forming the humidity-sensitive membrane of humidity sensor using inkjet is a method for forming the humidity-sensitive membrane by discharging polyelectrolyte ink from head of inkjet printer to the electrode-formed base material according to the pattern designed by a computer. According to this process, in case of the humidity-sensitive membrane which shows the accurate properties in respective humidity ranges, it is possible to selectively spread the humidity-sensitive membranes having different compositions on several electrodeson a single base material.

The process for forming the humidity-sensitive membrane using inkjet can solve all of the above-mentioned problems, and further, has the advantage of readily spreading the membrane on a circuit with controlling a thickness according as development of computers and peripherals. Further, this process makes the diversification of the humidity-sensitive membrane in a small amount in compliance of the consumer's demand possible, and thus, can provide the humidity sensors to the consumers at a low cost, and further, can provide the accurate and reliable humidity sensor.

In order to enhance the above-mentioned advantages, the polyelectrolyte solution must satisfy the requirements to make the inkjet printing possible, and do not have a lowering of humidity-sensitive property. That is, it must satisfy the properties to make the inkjet printing possible, including viscosity, surface tension and long-term storage stability, etc., and further, have a good humidity-sensitive property.

To overcome the above-mentioned problems, the present invention prepares a solution of polyelectrolyte composition, which is suitable for inkjet printing and has a good humidity-sensitive property, and provides an ink prepared therefrom, and further, provides a process for preparing the humidity sensor spread with the humidity-sensitive membrane using such an ink by means of the inkjet printer.

The present inventors have made the effort to develop the polyelectrolyte ink capable of forming the humidity-sensitive membrane in the inkjet manner as mentioned above. As a result thereof, we have prepared a suitable solution of polyelectrolyte composition for forming the humidity-sensitive membrane, from which the polyelectrolyte ink could then be prepared.

Said polyelectrolyte composition for forming the humidity-sensitive membrane is composed of a polyelectrolyte and a cross-linking agent. The organic solvent such as alcohols, alone or as a mixture thereof can be added to this composition to prepare the solution of polyelectrolyte composition.

Said polyelectrolyte is composed of as monomers a diamine-based compound, a dihaloalkane-based compound reactive with the diamine-based compound, and a compound capable of giving a reactive functional group by reacting with said two monomers.

The polyelectrolyte according to the prior art is generally prepared from copolymerization of vinyl monomers either containing quaternary ammonium salt or containing carboxy, sulfonate, sulfonium, phosphonium, phosphate salt, etc. with other several monomers. However, according to this since it is difficult to control the molecular weight, it is impossible to adjust the viscosity to that required for the ink.

The polyelectrolyte ink must satisfy the properties of ink to make the inkjet printing possible, that is, viscosity, surface tension and stability. To satisfy such requirements the low molecular polyelectrolyte having a cross-linkable functional group is suitable. The reason thereof is that polyelectrolyte having high molecular weight cannot play a function as the ink due to its high viscosity.

Said diamine-based compounds can be those selected from the group consisting of N,N,N',N'-tetramethylaminoethane, N,N,N',N'-tetraethylaminoethane, N,N,N',N'-tetramethyl-1,3-propanediamine, N,N,N',N'-tetraethyl-1,3-propanediamine, N,N,N',N'-tetramethyl-1,4-butane diamine, N,N,N',N'-tetraethyl-1,4-butanediariine, N,N,N',N'-tetramethyl-2-butene-1,4-diamine, N,N,N',N'-tetraethyl-2-butene-1,4-diamine, 1,3-bis(dimethylamino)-2-propanol, 1,3-bis(diethylamino)-2-propanol, N,N,N',N'-tetramethyl-1,3-diaminobutane, N,N,N',N'-tetraethyl-1,3-diaminobutane, 1,3-di(4-pyridyl)propane, 4,4'-bipyridyl, 2,2'-bipyridyl, 1,4-diazabicyclo[2,2,2]octane, N,N'-dimethypiperazine, N,N'-dimethyl-1,3-di(4-piperidyl)propane, pyrazine, pyrazine amide, 4-(N,N'-dimethylamino)pyridine, N,N,N',N'-tetramethyl-1,5-pentanediamine, N,N,N',N'-tetraethyl-1,5-pentanediamine, N,N,N',N'-tetramethyl-1,6-hexanediamine, N,N,N',N'-tetraethyl-1,6-hexanediamine, and a mixture of two or more of them.

Said dihaloalkanes reactive with the diamine-containing monomer can be those selected from the group consisting of the compounds containing two halogen atoms such as chlorine, bromine and iodine in alkyl group having 1 to 18 carbon atoms, the cyclic compounds having 5 to 6 carbon atoms and containing two halogen atoms and a mixture of two or more of them, such as 1,4-dichloro-2-butene, 1,4-dibromo-2-butene, 1,3-dichloro-2-propanol, 1,3-dibromo-2-propanol, 2,3-dichloropropanol, 1,3-dichloropropanon, 1,3-dibromopropanon, 1,4-dichloro-2-butanol, bis-2-chloroethyl ether, bis-2-bromoethyl ether, 1,2-bis(2-chloroethoxy)ethane, 1,2-bis(2-bromoethoxy)ethane, 1,3-dichloroacetone, 1,3-dibromoacetone, α, α'-dichloro-o-xylene, α, α'-dichloro-m-xylene, α, α'-dichloro-p-xylene, α, α'-dibromo-o-xylene, α, α'-dibromo-m-xylene and α, α'-dichloro-p-xylene.

As said compounds capable of giving a reactive functional group by reacting with said two monomers, each of halogen-containing alcohols or halogen-containing carboxylic acids or a mixture thereof can be used. For this purpose, halogen-containing alcohols can be selected from the group consisting of alcohol compounds containing one halogen atom such as chlorine, bromine or iodine in alkyl group having 2 to 18 carbon atoms; amine-containing alcohols can be selected from the group consisting of 2-aminoethanol, 3-aminopropanol, 2-aminopropanol, amino-2-propanol, aminobutanol, aminocyclohexanol, 2-(ethylamino)ethanol, 2-(methylamino)ethanol, diethanolamine, triethanolamine, N,N-dimethylaminoethanol, N,N-diethylaminoethanol, N,N-dibutylaminoethanol, N,N-dimethylaminopropanol, N,N-diethylaminopropanol, 3-pyrrolidinol, 1-methyl-3-pyrrolidinol, 1-methyl-2-pyrrolidylethanol, 3-hydroxypiperidine, 4-hydroxypiperidine, 1-(2-hydroxyethyl)piperzine and a mixture of two or more of them; halogen-containing carboxylic acids can be selected from the group consisting of carboxylic acids containing one halogen atom such as chlorine, bromine or iodine in alkyl group having 2 to 18 carbon atoms or a mixture of two or more of them; and amine-containing carboxylic acids can be selected from the group consisting of amino acids containing 2 to 18 carbon atoms and a mixture of two or more of them.

As a cross-linking agent which can be reacted with said reactive functional group, one selected from the group consisting of diisocyanate, methylol melamine, methylol urea, blocked isocyanate, aziridine, oxazoline, epoxy, diaminoalkane and carbodiimide cross-linking agents can be used.

As described above, the polyelectrolyte is composed of as monomers the diamine-based compound, the dihaloalkane-based compound reactive with the diamine-based compound, the compound capable of giving a reactive functional group by reacting with said two monomers, and the cross-linking agent which can be reacted with said reactive functional group. To this composition the organic solvent such as alcohols, alone or as a mixture thereof can be added to prepare the solution of polyelectrolyte composition.

To the solution of polyelectrolyte composition prepared according to the above process an organic solvent, such as alcohols, to ensure the liquid fluidity suitable for inkjet printer, a high boiling humectant to prevent the drying of ink nozzle, and a surfactant are added to prepare a conductive ink.

The polyelectrolyte ink composition of the present invention is composed of the solution of polyelectrolyte composition of 10-50 wt %, preferably of 15-40 wt %, more preferably of 20-30 wt %, the cross-linking agent of 1-10 wt %, the humectant compatible with cross-linking agent of 40-80 wt %, preferably of 40-70 wt %, more preferably of 50-70 wt %, and the non-ionic and ionic surfactant of 0.1-2 wt %, preferably of 0.2-1 wt %, more preferably of 0.5-1 wt %.

For this use, a polar solvent having boiling point of 50-300° C., preferably 60-200° C., more preferably 60-150° C. alone or a mixture of two or more thereof can be used as the organic solvent.

When the boiling point of the solvent is lower than 100° C., clogging of inkjet head nozzle may be caused, and cracking or roughening of the surface may present after the humidity-sensitive membrane is formed.

Further, the amount of solvent play a role of controlling the viscosity and can be adjusted in consideration of thickness of the membrane, size of inkjet head nozzle, etc. In this case, the viscosity is desirably in the range of 2-100 cps, preferably in the range of 2-50 cps, and more preferably in the range of 2-35 cps.

The surfactant is not limited to any one of ionic and non-ionic surfactants, and can be used alone or in the form of a mixture of two or more surfactants. It is used for the purpose of controlling the surface tension of the surface of base material, i.e. of controlling the wettability of ink to the base material. In general, it can be preferably used so that the surface tension can be controlled to 32-50 dyne/cm.

If the surface tension is lower than 32 dyne/cm, the resolution as required cannot be maintained since the composition is too rapidly spread over the base material after injecting to the base material. If the surface tension is higher than 50 dyne/cm, the amount of ink injected from nozzle is not so sufficient as required, and therefore, a sufficient thickness of the membrane cannot be obtained.

The methods for forming the humidity-sensitive membrane include a piezo mode which uses the piezo-electric element to inject ink droplets by vibration thereof, a thermal mode wherein ink droplets are pushed out as bubbles are generated inside by heat, and a bubble jet mode. However, when inks are injected by means of heat, the decomposition of electrolyte may be caused to induce the clogging of nozzle or the lowering of a stability of the solution.

In the present invention, it is preferred to use inkjet nozzle according to the piezo mode, more preferably to use the inkjet print equipment which makes the control of frequency, the control of temperature at ink reservoir, the control of nozzle size, and the control of temperature of applied base material possible.

The humidity-sensitive membrane formed by means of the inkjet injection mode as above is treated with heat to obtain the final humidity-sensitive property. In this case, the appearance features, adhesive property and cross-linking density of the membrane can be varied depending on the conditions of heat treatment.

For this purpose, the temperature for heat treatment at which the polyelectrolyte solution can be spread and cross-linked is desirably 50-20° C., preferably 60-150° C., and more preferably 60-130° C.

The heat treatment can be conventionally carried out at 60-100° C. for 10-30 minutes and then at 100-130° C. for 10-30 minutes, under atmospheres of nitrogen, argon, hydrogen alone or a mixed gas thereof, to provide the improvement of properties and humidity-sensitive property of the membrane.

The humidity-sensitive membrane prepared according to the present invention show the resistance of 1 to 3 MΩ at 30% RH and 1 to 5 kΩ at 90% RH.

DESCRIPTION OF THE SYMBOLS FOR MAIN PORTIONS OF THE DRAWINGS

Figure 1:
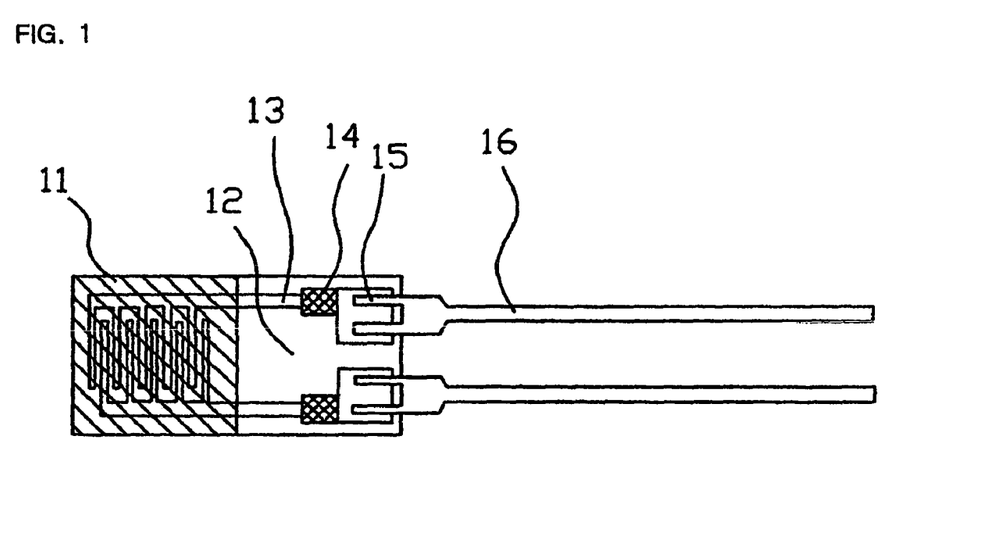
FIG. 1 is a front view of an alumina board humidity sensor with humidity-sensitive membrane thereon.
Figure 2:
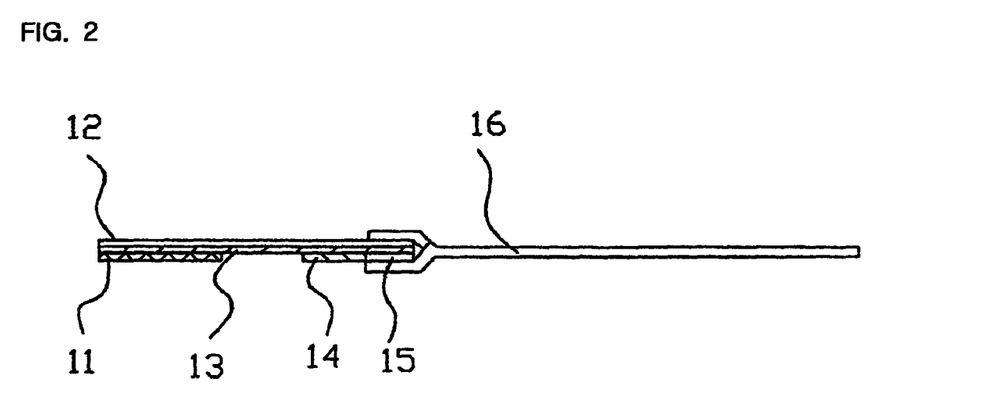
FIG. 2 is a side view of FIG. 1.
Figure 3:
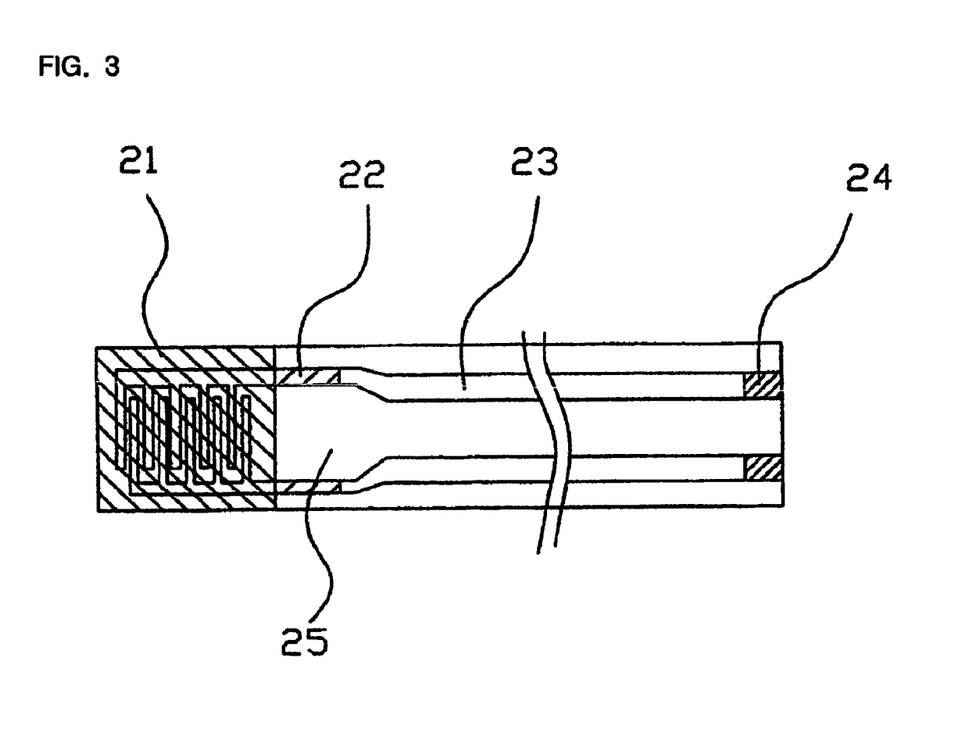
FIG. 3 is a front view of a polyimide board humidity sensor with humidity-sensitive membrane thereon.
Figure 4:
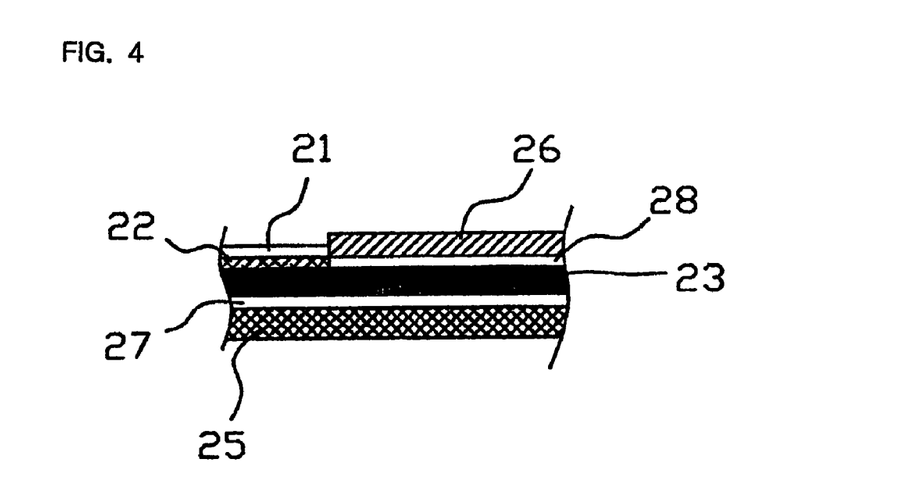
FIG. 4 is a side view of FIG. 3.

| 11, 21: Humidity-sensitive membrane | 12: Ceramic board |
| 13, 22: Gold electrode | |
| 14: Electrode protective membrane | |
| 15, 24: Electrode pad | 16: Lead frame |
| 23: Copper electrode | 25: Base film |
| 26: Coverlay film | 27: Adhesive |
| 28: Coverlay adhesive | |

Best Mode for Carrying Out the Invention

The present invention on the basis of the above described matters will be more specifically explained in the following examples and comparative examples. However, it should be understood that the present invention is not limited by the following examples in any manner.

Polyimide FPC Electrode

A flexible FPC (flexible printed circuit) board which can be adhered to the curved surface has advantages in that it can be used with bending, and the print circuit board itself is small due to the realization of a single tri-dimensional wiring and the omission of connector and wire, and therefore, the miniaturization and light-weight of the electronic equipments themselves and the cost reduction thereof can be provided. The other characteristics of FPC board are that since the board is thin and light, in case where the base film having a thickness of 25 μm is used a total thickness of the board is about 100-140 μm, and therefore, the volume and weight thereof get to be small, and further, it is possible to miniaturize the whole equipment. However, since the base material is thin and therefore, has a low mechanical strength, it may be damaged. Such disadvantages can be complemented by attaching the reinforcing plate and the coverlay as the unique structures of FPC. The electrode was prepared in the shape of a linear byte, wherein a total of 5 bytes are present at the interval of 0.25 mm.

As the material for electrodes copper was used with gold plating having a thickness of 0.5 μm. The structure of FPC was constituted by the board, copper foil, coverlay film and reinforcing plate. The joint portion of the terminal part was prepared by covering with nickel plating of 2 μm and gold plating of 1 μm for easy soldering. The surface of copper foil is a plane and a flexible, rolled copper foil having a thickness of 35 μm was used as the copper foil for current capacity and bending application. In addition, for corrosive property and protection of copper foil other polyimide film having a thickness of 35 μm was applied as the coverlay to other areas than the humidity-sensitive area.

Alumina Board Electrode

The board used as the sensor was alumina in the form of 96% α-alumina. 10×5 Electrodes in the size of 5 mm×10 mm were simultaneously formed on the board (50 mm×50 mm×5 mm) generally used in the thick film circuit. To prepare the conductive electrode gold paste was used on which comb pattern was formed at intervals of 0.195 mm and 0.4 mm. The portion for soldering used Ag—Pd (6:1) paste, and the glass overcoat was used to prevent the migration of gold electrode. After printing, the electrode was dried in a drying oven at 150° C. for 15 minutes to remove the solvent and binder contained in the paste and then finished by sintering in Muffle electric furnace at 850° C. for 10 minutes for electrode burning.

Further, electrical properties were examined for the resulting humidity sensor. For the humidity sensitive property of the resulting humidity sensor, the resistance value was determined by controlling the humidity at the power of LCR meter (ED-Lab. Korea, Model EDC-1630) of 1 kHz, 1 V when the constant temperature and humidity chamber (JEIO TECH, TM-NFM-L (−20° C.~100° C.)) is equilibrated at temperature of 25° C. and relative humidity of 30% RH. For respective test samples, 50 test samples having the same composition were prepared and measured. The humidity sensitive property of the sensor as obtained using the same composition was plotted and then, the area between the maximum and minimum values was plotted to determine the error range.

Hereinafter, preferred examples of the present invention and comparative examples will be illustrated.

The following examples are provided for explaining the present invention but should not be construed to limit the scope of the present invention.

Example 1

N,N,N',N'-tetramethyl-1,4-diaminobutane (14.40 g, 100 mmol) dissolved in 2-ethoxyethanol (50 g) was introduced into a round-bottomed flask equipped with a condenser. After 2-bromonoethanol (1.25 g, 10 mmol) dissolved in 2-ethoxyethanol (50 g) was added dropwise while maintaining temperature below 5° C., the reaction was progressed at 60° C. for 4 hours. After the temperature is elevated to 80° C., the reaction was continued for 24 hours and then the solvent was evaporated to remove by about 50 g. 30 g of dimethylsulfoxide was added to the final solution and then blocked diisocyanate (1.5 g) was dissolved therein to prepare the final solution of polyelectrolyte composition. According to this process, the colorless humidity sensitive solution having the final solid content of 33.0% could be obtained.

To 15 g of the polyelectrolyte solution of Example 1 above were added 5 g of isopropyl alcohol and 0.001 g of sulfinol-465 (trade name; prepared by Air Products Co.) to prepare the ink for inkjet. In this ink, the solid content was 25.0%, the surface tension was 37 dyne/cm, and the viscosity was 15 cps.

Example 2

N,N,N',N'-tetramethyl-1,6-diaminohexane (15.51 g, 90 mmol) and 2-(N,N-dimethylamino)ethanol (0.89 g, 10 mmol) dissolved in 2-ethoxyethanol (50 g) were introduced into a round-bottomed flask equipped with a condenser. After 1,4-dibromobutane (21.59 g, 100 mmol) dissolved in 2-ethoxyethanol (50 g) was added dropwise while maintaining temperature below 5° C., the reaction was progressed at 60° C. for 4 hours. After the temperature is elevated to 80° C., the reaction was continued for 24 hours and then the solvent was evaporated to remove by about 50 g. 30 g of dimethylsulfoxide was added to the final solution and then blocked diisocyanate (1.5 g) was dissolved therein to prepare the final solution of polyelectrolyte composition. According to this process, the colorless humidity sensitive solution having the final solid content of 33.0% could be obtained.

To 15 g of the polyelectrolyte solution of Example 2 above were added 5 g of isopropyl alcohol and 0.001 g of sulfinol-465 (trade name; prepared by Air Products Co.) to prepare the ink for inkjet. In this ink, the solid content was 25.0%, the surface tension was 36 dyne/cm, and the viscosity was 13 cps.

Example 3

N,N,N',N'-tetramethyl-1,4-diaminobutane (13.68 g, 95 mmol) and N,N,N',N'-tetramethyl-1,3-diamino-2-propanol (0.23 g, 5 mmol) dissolved in 2-ethoxyethanol (50 g) were introduced into a round-bottomed flask equipped with a condenser. After 1,6-dibromohexane (21.90 g, 100 mmol) dissolved in 2-ethoxyethanol (50 g) was added dropwise while maintaining temperature below 5° C., the reaction was progressed at 60° C. for 4 hours. After the temperature is elevated to 80° C., the reaction was continued for 24 hours and then the solvent was evaporated to remove by about 50 g. 30 g of dimethylsulfoxide was added to the final solution and then blocked diisocyanate (1.5 g) was dissolved therein to prepare the final solution of polyelectrolyte composition. According to this process, the colorless humidity sensitive solution having the final solid content of 31.8% could be obtained.

To 15 g of the polyelectrolyte solution of Example 3 above were added 5 g of isopropyl alcohol and 0.001 g of sulfinol-465 (trade name; prepared by Air Products Co.) to prepare the ink for iniyet In this ink, the solid content was 23.9%, the surface tension was 37 dyne/cm, and the viscosity was 14 cps.

Example 4

N,N,N',N'-tetramethyl-1,6-diaminohexane (17.23 g, 100 mmol) dissolved in 2-ethoxyethanol (50 g) was introduced into a round-bottomed flask equipped with a condenser. After 1,4-dibromobutane (20.51 g, 95 mmol) and 1,3-dibromo-2-propanol (1.09 g, 5 mmol) dissolved in 2-ethoxyethanol (50 g) were added dropwise while maintaining temperature below 5° C., the reaction was progressed at 60° C. for 4 hours. After the temperature is elevated to 80° C., the reaction was continued for 24 hours and then the solvent was evaporated to remove by about 50 g. 30 g of dimethylsulfoxide was added to the final solution and then blocked diisocyanate (1.5 g) was dissolved therein to prepare the final solution of polyelectrolyte composition. According to this process, the colorless humidity sensitive solution having the final solid content of 33.5% could be obtained.

To 15 g of the polyelectrolyte solution of Example 4 above were added 5 g of isopropyl alcohol and 0.001 g of sulfinol-465 (trade name; prepared by Air Products Co.) to prepare the ink for inkjet. In this ink, the solid content was 25.2%, the surface tension was 36 dyne/cm, and the viscosity was 13 cps.

Examples 5-8

The inks prepared from the above Examples 1 to 4 were filled in a polyethylene container, and then printed 5 times on the sensor electrode in which the electrode was formed on alumina board or polyimide film, using a plate printer equipped with the inkjet printer head F076000 (trade name; prepared by Epson, Inc.) of a piezo mode and treated with heat to obtain the humidity sensor. In this step, the heat treatment conditions include the treatment at 100° C. for 30 minutes and subsequently at 120° C. for 30 minutes. The characteristic properties of respective electrodes after heat treatment are specifically presented in the following Tables 1 and 2.

Comparative Example 1

The 4-membered high polymer comprising methyl methacrylate, acrylic acid, hydroxylethyl methacrylate and dimethyl ammonium ethyl methacrylate chloride salt in the weight ratio of 40/2/0.5/57.5 was dissolved in 2-methoxyethanol to prepare the polyelectrolyte solution for dipping. From this process, the final polyelectrolyte solution could be obtained in the form of a colorless solution having a solid content of 10.5% and a viscosity of 230 cps/25° C. 0.1 wt % of XAMA-7 (trade name; prepared by Zeneca Corporation) was mixed with 100 wt % of the resulting solution to prepare the humidity sensitive solution, which was then applied to Kapton (trade name; prepared by DuPont Co.) as alumina board or polyimidie film on which the electrode is formed, by dipping process to form the humidity-sensitive membrane.

Comparative Example 2

The 4-membered high polymer comprising styrene, acrylic acid, hydroxyl ethyl methacrylate and dimethyl ammonium ethyl methacrylate chloride salt in the weight ratio of 40/2/0.5/57.5 was dissolved in 2-methoxyethanol to prepare the polyelectrolyte solution for dipping. From this process, the final polyelectrolyte solution could be obtained in the form of a colorless solution having a solid content of 12.0% and a viscosity of 450 cps/25° C. 0.1 wt % of XAMA-7 (trade name; prepared by Zeneca Corporation) was mixed with 100 wt % of the resulting solution to prepare the humidity sensitive solution, which was then applied to Kapton (trade name; prepared by DuPont Co.) as alumina board or polyimidie film on which the electrode is formed, by dipping process to form the humidity-sensitive membrane.

TABLE 1

Humidity sensor using alumina electrode

| | Resistance, Ω | | | | | | | Error |
|---|---|---|---|---|---|---|---|---|
| | 30% RH | 40% RH | 50% RH | 60% RH | 70% RH | 80% RH | 90% RH | (±% RH) |
| Example 5 | 2790000 | 803000 | 261000 | 107000 | 40300 | 10300 | 2700 | 0.37 |
| Example 6 | 3330000 | 1026000 | 369000 | 129600 | 41400 | 14800 | 3500 | 0.42 |

TABLE 1-continued

Humidity sensor using alumina electrode

| | Resistance, Ω | | | | | | | Error |
|---|---|---|---|---|---|---|---|---|
| | 30% RH | 40% RH | 50% RH | 60% RH | 70% RH | 80% RH | 90% RH | (±% RH) |
| Example 7 | 3780000 | 1260000 | 441000 | 161500 | 45700 | 17100 | 4400 | 0.39 |
| Example 8 | 1890000 | 639000 | 201000 | 78300 | 27900 | 8500 | 2100 | 0.41 |
| comparative Example 1 | 4500000 | 1500000 | 440000 | 154000 | 43000 | 15500 | 4100 | 2.90 |
| comparative Example 2 | 4900000 | 2100000 | 591000 | 199500 | 55800 | 21000 | 5400 | 3.10 |

TABLE 2

Humidity sensor using polyimide electrode

| | Resistance, Ω | | | | | | | Error |
|---|---|---|---|---|---|---|---|---|
| | 30% RH | 40% RH | 50% RH | 60% RH | 70% RH | 80% RH | 90% RH | (±% RH) |
| Example 5 | 2500000 | 720000 | 230000 | 96000 | 36000 | 9300 | 2500 | 0.29 |
| Example 6 | 2900000 | 920000 | 330000 | 116000 | 37000 | 13000 | 3200 | 0.30 |
| Example 7 | 3400000 | 1100000 | 390000 | 140000 | 40000 | 15000 | 4000 | 0.32 |
| Example 8 | 1700000 | 570000 | 180000 | 70000 | 25000 | 7650 | 1900 | 0.36 |
| comparative Example 1 | 3800000 | 1200000 | 374000 | 130000 | 36000 | 13000 | 3500 | 3.70 |
| comparative Example 2 | 4100000 | 1700000 | 502000 | 169000 | 47000 | 17000 | 4600 | 3.30 |

Although the sensors obtained from Examples 5 to 8 show different humidity sensitive properties from each other due to a difference between chemical compositions of the humidity sensitive membranes, they show an excellent humidity sensitive property sufficient for common availability in a semi-log graph. The inks forming the humidity sensitive membrane were examined after 5 times printing. As a result, it could be identified that when the thickness of the humidity sensitive membrane is thin, then the resistance is increased, whereas when the thickness is thick, then the resistance is lowered. The formation of the humidity sensitive membrane using inkjet has also the advantage in that by controlling the numbers of printing the thickness of the humidity sensitive membrane can be controlled and the humidity sensitive property can also be controlled. In the reproduction accuracy between 50 sensor thus prepared, it could be seen that all of the humidity sensors prepared by printing belong to the range of ±0.5% RH, and therefore, show a high product reproducibility. Contrary to this, it could also be seen that the sensors prepared by dipping method which has been conventionally used for preparing the prior humidity falls within the range of ±3% RH, and therefore, shows lower product reproducibility than the inkjet printing mode. In addition, in case of polyimide electrode the sensors obtained by dipping method were not easy to dip several sensors at the same time due to a flexibility of the board and therefore, showed that the reproduction error of the samples thus prepared is more greatly deviated. However, in case of the sensors obtained by inkjet mode it could be seen that the reproduction error between the samples is close to the range of ±0.3% RH regardless of the quality of materials and therefore, a very high product reproducibility can be assured.

INDUSTRIAL APPLICABILITY

According to the above-mentioned result, the present invention provides the polyelectrolyte solution having the properties, including viscosity, solid content and inkjet dischargeability, suitable for use as the humidity sensitive membrane of the humidity sensor, and the process for preparing the polyelectrolyte solution for inkjet. Thus, the humidity sensitive membrane having properties which are not beyond the properties of the prior humidity sensor, and having a regular thickness in comparison to the conventional mode, after heat treatment via inkjet printing process could be formed. Further, the present invention could provide the technology for preparing the humidity sensor having high product reliability.

The invention claimed is:

1. A polyelectrolyte composition for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups, wherein the at least one compound containing cross-linking functional groups is a compound selected from the group consisting of halogen-containing carboxylic acids, amine-containing alcohols and amine-containing carboxylic acids, or a mixture thereof.

2. The polyelectrolyte composition according to claim 1, wherein the diamine-based compound is a compound selected from the group consisting of N,N,N',N'-tetramethylaminoethane, N,N,N',N'-tetraethylaminoethane, N,N,N',N'-tetramethyl-1,3-propanediamine, N,N,N',N'-tetraethyl-1,3-propanediamine, N,N,N',N'-tetramethyl-1,4-butanediamine, N,N,N',N'-tetraethyl-1,4-butanediamine, N,N,N',N'-tetramethyl-2-butene-1,4-diamine, N,N,N',N'-tetraethyl-2-butene-1,4-diamine, 1,3-bis(dimethylamino)-2-propanol, 1,3-bis(diethylamino)-2-propanol, N,N,N',N'-tetramethyl-1,3-diaminobutane, N,N,N',N'-tetraethyl-1,3-diaminobutane, 1,3-di(4-pyridyl)propane, 4,4'-bipyridyl, 2,2'-bipyridyl, 1,4-diazabicyclo[2,2,2]octane, N,N'-dimethylpiperazine, N,N'-dimethyl-1,3-di(4-piperidyl)propane, pyrazine, pyrazine amide, 4-(N,N'-dimethylamino)pyridine, N,N,N',N'-tetramethyl-1,5-pentanediamine, N,N,N',N'-tetraethyl-1,5-pentanediamine, N,N,N',N'-tetramethyl-1,6-hexanediamine and N,N,N',N'-tetraethyl-1,6-hexanediamine, or a mixture of two or more of them.

3. The polyelectrolyte composition according to claim 1, wherein the dihaloalkane is a compound selected from the group consisting of compounds containing two halogen atoms, in alkyl group having 1 to 18 carbon atoms, cyclic compounds having 5 to 6 carbon atoms and containing two halogen atoms and a mixture of two or more of them.

4. The polyelectrolyte composition according to claim 3, wherein the halogen atom is selected from the group consisting of chlorine, bromine and iodine.

5. The polyelectrolyte composition according to claim 3, wherein the dihaloalkane is selected from the group consisting of 1,4-dichloro-2-butene, 1,4-dibromo-2-butene, 1,3-dichloro-2-propanol, 1,3-dibromo-2-propanol, 2,3-dichloropropanol, 1,3-dichloropropanon, 1,3-dibromopropanon, 1,4-dichloro-2-butanol, bis-2-chloroethyl ether, bis-2-bromoethyl ether, 1,2-bis(2-chloroethoxy)ethane, 1,2-bis(2-bromoethoxy)ethane, 1,3-dichloroacetone, 1,3-dibromoacetone, α,α'-dichloro-o-xylene, α,α'-dichloro-m-xylene, α,α'-dichloro-p-xylene, α,α'-dibromo-o-xylene, α,α'-dibromo-m-xylene and α,α'-dichloro-p-xylene.

6. The polyelectrolyte composition according to claim 1, wherein the amine-containing alcohol is a compound selected from the group consisting of 2-aminoethanol, 3-aminopropanol, 2-aminopropanol, amino-2-propanol, aminobutanol, aminocyclohexanol, 2-(ethylamino)ethanol, 2-(methylamino)ethanol, diethanolamine, triethanolamine, N,N-dimethylaminoethanol, N,N-diethylaminoethanol, N,N-dibutylaminoethanol, N,N-dimethylaminopropanol, N,N-diethylaminopropanol, 3-pyrrolidinol, 1-methyl-3-pyrrolidinol, 1-methyl-2-pyrrolidylethanol, 3-hydroxypiperidine, 4-hydroxypiperidine, and 1-(2-hydroxyethyl)piperazine, or a mixture thereof.

7. The polyelectrolyte composition according to claim 1, wherein the halogen-containing carboxylic acid is a compound selected from the group consisting of carboxylic acids containing one halogen atom and having 2 to 18 carbon atoms, or a mixture thereof.

8. The polyelectrolyte composition according to claim 7, wherein the halogen atom is selected from the group consisting of chlorine, bromine and iodine.

9. The polyelectrolyte composition according to claim 1, wherein the amine-containing carboxylic acid is a compound selected from the group consisting of amino acids containing 2 to 18 carbon atoms, or a mixture thereof.

10. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant.

11. The polyelectrolyte ink according to claim 10, wherein the cross-linking agent is selected from the group consisting of diisocyanate, methylol melamine, methylol urea, blocked isocyanate, aziridine, oxazoline, epoxy, diaminoalkane and carbodiimide cross-linking agent.

12. A process for preparing a humidity sensor, wherein a polyelectrolyte ink is spread using an inkjet printing mode and then treated with heat to form a humidity sensitive membrane, wherein a polyelectrolyte ink comprising 10-50 wt % of a polyelectrolyte composition having 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant is spread on a board having electrodes thereon and then treated with heat at 50-200° C. to form the humidity sensitive membrane.

13. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant, wherein the diamine-based compound is a compound selected from the group consisting of N,N,N',N'-tetramethylaminoethane, N,N,N',N'-tetraethylamino ethane, N,N,N',N'-tetramethyl-1,3-propanediamine, N,N,N',N'-tetraethyl-1,3-propanediamine, N,N,N',N'-tetramethyl-1,4-butanediamine, N,N,N',N'-tetraethyl-1,4-butanediamine, N,N,N',N'-tetramethyl-2-butene-1,4-diamine, N,N,N',N'-tetraethyl-2-butene-1,4-diamine, 1,3-bis(dimethylamino)-2-propanol, 1,3-bis(diethylamino)-2-propanol, N,N,N',N'-tetramethyl-1,3-diaminobutane, N,N,N',N'-tetraethyl-1,3-diaminobutane, 1,3-di(4-pyridyl)propane, 4,4'-bipyridyl, 2,2'-bipyridyl, 1,4-diazabicyclo [2,2,2]octane, N,N'-dimethylpiperazine, N,N'-dimethyl-1,3-di(4-piperidyl)propane, pyrazine, pyrazine amide 4-N,N'-dimethlamino)pyridine N,N,N',N'-tetramethyl-1,5-pentanediamine, N,N,N',N'-tetraethyl-1,5-pentanediamine, N,N,N',N'-tetramethyl-1,6-hexanediamine and N,N,N',N'-tetraethyl-1,6-hexanediamine, or a mixture of two or more of them.

14. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant, wherein the dihaloalkane is a compound selected from the group consisting of compounds containing two halogen atoms in alkyl group having 1 to 18 carbon atoms, cyclic compounds having 5 to 6 carbon atoms and containing two halogen atoms and a mixture of two or more of them.

15. The polyelectrolyte ink according to claim 14, wherein the halogen atom is selected from the group consisting of chlorine, bromine and iodine.

16. The polyelectrolyte ink according to claim 14, wherein the dihaloalkane is selected from the group consisting of 1,4-dichloro-2-butene, 1,4-dibromo-2-butene, 1,3-dichloro-2-propanol, 1,3-dibromo-2-propanol, 2,3-dichloropropanol, 1,3-dichloropropanon, 1,3-dibromopropanon, 1,4-dichloro-2-butanol, bis-2-chloroethyl ether, bis-2-bromoethyl ether, 1,2-bis(2-chloroethoxy)ethane, 1,2-bis(2-bromoethoxy)ethane, 1,3-dichloroacetone, 1,3-dibromoacetone, α,α'-dichloro-o-xylene, α,α'-dichloro-m-xylene, α,α'-dichloro-p-xylene, α,α'-dibromo-o-xylene, α,α'-dibromo-m-xylene and α,α'-dichloro-p-xylene.

17. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant, wherein the at least one compound containing cross-linking functional groups is a compound selected from the group consisting of halogen-containing alcohols, halogen-containing carboxylic acids, amine-containing alcohols and amine-containing carboxylic acids, or a mixture thereof.

18. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant, wherein the at least one compound containing cross-linking functional groups is a compound selected from the group consisting of halogen-containing alcohols, halogen-containing carboxylic acids, amine-containing alcohols and amine-containing carboxylic acids, or a mixture thereof, and wherein the halogen-containing alcohol is a compound selected from the group consisting of alcohol compounds containing one halogen atom in alkyl group having 2 to 18 carbon atoms or a mixture thereof and wherein the amine-containing alcohol is a compound selected from the group consisting of 2-aminoethanol, 3-aminopropanol, 2-aminopropanol, amino-2-propanol, aminobutanol, aminocyclohexanol, 2-(ethylamino)ethanol, 2-(methylamino)ethanol, diethanolamine, triethanolamine, N,N-dimethylaminoethanol, N,N-diethylaminoethanol, N,N-dibutylaminoethanol, N,N-dimethylaminopropanol, N,N-diethylaminopropanol, 3-pyrrolidinol, 1-methyl-3-pyrrolidinol, 1-methyl-2-pyrrolidylethanol, 3-hydroxypiperidine, 4-hydroxypiperidine, and 1-(2-hydroxyethyl)piperazine, or a mixture thereof.

19. The polyelectrolyte ink according to claim 18, wherein the halogen atom is selected from the group consisting of chlorine, bromine and iodine.

20. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant, wherein the at least one compound containing cross-linking functional groups is a compound selected from the group consisting of halogen-containing alcohols, halogen-containing carboxylic acids, amine-containing alcohols and amine-containing carboxylic acids, or a mixture thereof, and wherein the halogen-containing carboxylic acid is a compound selected from the group consisting of carboxylic acids containing one halogen atom and having 2 to 18 carbon atoms, or a mixture thereof.

21. The polyelectrolyte ink according to claim 20, wherein the halogen atom is selected from the group consisting of chlorine, bromine and iodine.

22. A polyelectrolyte ink, comprising 10-50 wt % of a polyelectrolyte composition, for a humidity sensitive membrane of a humidity sensor, comprising 35-50 wt % of at least one compound selected from diamine-based compounds, 45-64.9 wt % of at least one compound selected from dihaloalkane-based compounds, and 0.1-5 wt % of at least one compound containing cross-linking functional groups; 1-10 wt % of a cross-linking agent; 38-88.9 wt % of an organic solvent; and 0.1-2 wt % of a mixture of a non-ionic surfactant and an ionic surfactant, wherein the at least one compound containing cross-linking functional groups is a compound selected from the group consisting of halogen-containing alcohols, halogen-containing carboxylic acids, amine-containing alcohols and amine-containing carboxylic acids, or a mixture thereof, and wherein the amine-containing carboxylic acid is a compound selected from the group consisting of amino acids containing 2 to 18 carbon atoms, or a mixture thereof.

* * * * *

UNITED STATES PATENT AND TRADEMARK OFFICE
CERTIFICATE OF CORRECTION

| | | |
|---|---|---|
| PATENT NO. | : 7,771,620 B2 | Page 1 of 1 |
| APPLICATION NO. | : 10/567976 | |
| DATED | : August 10, 2010 | |
| INVENTOR(S) | : Chung et al. | |

It is certified that error appears in the above-identified patent and that said Letters Patent is hereby corrected as shown below:

Title Page, Item (54) Title, Line 2, and
Column 1, the Title, Line 2:

"HUMIDITY SENSER" should read -- HUMIDITY SENSOR --

Signed and Sealed this

Thirtieth Day of November, 2010

David J. Kappos
*Director of the United States Patent and Trademark Office*